US006689893B2

(12) United States Patent
Reddy et al.

(10) Patent No.: US 6,689,893 B2
(45) Date of Patent: Feb. 10, 2004

(54) SHELF STABLE HAZE FREE LIQUIDS OF OVERBASED ALKALINE EARTH METAL SALTS

(75) Inventors: James E. Reddy, Lyndhurst, OH (US); Chester E. Ramey, Chagrin Falls, OH (US); Lawrence A. Dominey, Chagrin Falls, OH (US)

(73) Assignee: OMG Americas, Inc., Westlake, OH (US)

( * ) Notice: Subject to any disclaimer, the term of this patent is extended or adjusted under 35 U.S.C. 154(b) by 225 days.

(21) Appl. No.: 09/861,393

(22) Filed: May 18, 2001

(65) Prior Publication Data

US 2003/0050490 A1 Mar. 13, 2003

(51) Int. Cl.$^7$ ................................................ C07C 51/00
(52) U.S. Cl. ........................................ 554/156; 554/157
(58) Field of Search ................................. 554/156, 157

(56) References Cited

U.S. PATENT DOCUMENTS

| | | | |
|---|---|---|---|
| 2,616,904 A | 11/1952 | Asseff et al. ................ 260/399 |
| 2,760,970 A | 8/1956 | Le Suer ....................... 260/429 |
| 2,767,164 A | 10/1956 | Asseff et al. ................ 260/139 |
| 2,798,852 A | 7/1957 | Wiese et al. ................. 252/42.7 |
| 2,802,816 A | 8/1957 | Asseff et al. ................ 260/139 |
| 2,971,014 A | 2/1961 | Mastin ........................ 260/398 |
| 2,989,463 A | 6/1961 | Mastin ......................... 252/25 |
| 3,027,325 A | 3/1962 | McMillen et al. ............. 252/33 |
| 3,031,284 A | 4/1962 | Andress, Jr. et al. ........... 44/76 |
| 3,147,232 A | 9/1964 | Norman et al. ................ 260/23 |
| 3,194,823 A | 7/1965 | Le Suer et al. .............. 260/414 |
| 3,342,733 A | 9/1967 | Robbins et al. ................ 252/33 |
| 3,533,975 A | 10/1970 | Scullin ........................ 260/23 |
| 3,773,664 A | 11/1973 | Lesuer ....................... 252/40.7 |
| 3,779,922 A | 12/1973 | LeSuer ....................... 252/34.7 |
| 4,159,973 A | 7/1979 | Hoch et al. ............. 260/23 XA |
| 4,252,698 A | 2/1981 | Ito et al. ................. 260/18 EP |
| 4,665,117 A * | 5/1987 | Quinn |
| 5,147,917 A | 9/1992 | Sugawara et al. ........... 524/257 |
| 5,259,966 A | 11/1993 | Burke, Jr. et al. ............ 252/18 |
| 5,322,872 A | 6/1994 | Quinn ........................ 524/186 |
| 5,519,076 A * | 5/1996 | Odaira et al. |
| 5,830,935 A * | 11/1998 | Khattar et al. |
| 5,859,267 A * | 1/1999 | Khattar et al. |

FOREIGN PATENT DOCUMENTS

| WO | 99/10307 | * 3/1999 | |
| WO | WO 99/10307 | 3/1999 | ........... C07C/51/41 |

* cited by examiner

Primary Examiner—Deborah D. Carr
(74) Attorney, Agent, or Firm—Wood, Herron & Evans, L.L.P.

(57) ABSTRACT

Shelf stable haze free liquids of overbased alkaline earth metal salts are obtained by reacting metal base with fatty acids in the presence of liquid hydrocarbon and aliphatic alcohols having at least 8 carbon atoms to provide overbased liquids essentially free of a phenol or a phenolic derivative. Stabilizer compositions containing the overbased liquids and mixed metal stabilizers of zinc, cadmium and tin are provided for stabilizing halogen-containing polymers.

44 Claims, No Drawings

SHELF STABLE HAZE FREE LIQUIDS OF OVERBASED ALKALINE EARTH METAL SALTS

FIELD OF THE INVENTION

The present invention relates to a shelf stable haze free liquid of an alkaline earth metal salt of a fatty acid and a process of producing the liquids. Mixed metal stabilizers containing the overbased liquids and metal carboxylates of zinc, cadmium or alkyltin are provided and used as stabilizers for halogen-containing polymers such as polyvinyl chloride (PVC).

BACKGROUND OF THE INVENTION

The preparation of overbased calcium or barium salts of carboxylic acids, alkyl phenols, and sulfonic acids are disclosed in the following U.S. Pat. Nos. 2,616,904; 2,760,970; 2,767,164; 2,798,852; 2,802,816; 3,027,325; 3,031,284; 3,342,733; 3,533,975; 3,773,664; and 3,779,922. The use of these overbased metal salts in the halogen-containing organic polymer is described in the following U.S. Pat. Nos. 4,159,973; 4,252,698; and 3,194,823. The use of overbased barium salt in stabilizer formulations has increased during recent years. This is due, in the main, to the fact that overbased barium salts possess performance advantages over the neutral barium salts. The performance advantages associated with overbased barium salts are low plate-out, excellent color hold, good long-term heat stability performance, good compatibility with the stabilizer components, etc. Unfortunately, most of the overbased barium salts are dark in color and, while these dark colored overbased barium salts are effective stabilizers for halogen-containing organic polymer, their dark color results in the discoloration of the end product. This feature essentially prohibits the use of dark colored overbased barium salts in applications where a light colored polymer product is desired.

According to the teachings of U.S. Pat. No. 4,665,117, light colored alkali or alkaline earth metal salts are prepared where alkyl phenol is used as a promoter. However, alkyl phenol is also a major cause for the development of color in the final product. This problem is overcome by the use of propylene oxide which displaces the hydrogen of the phenolic hydroxyl group and thereby restricts the formation of colored species. However, there are disadvantages associated with this approach, principally due to the toxic nature of propylene oxide. Propylene oxide is classified as a possible carcinogen and laboratory animal inhalation studies have shown evidence of a link to cancer. Propylene oxide is also listed as a severe eye irritant, and prolonged exposure to propylene oxide vapors may result in permanent damage to the eye. Furthermore, propylene oxide is extremely flammable and explosive in nature under certain conditions. Propylene oxide boils at 94° F. and flashes at −20° F. As a result, extreme precautions are required to handle propylene oxide at the plant site. Special storage equipment is required for propylene oxide and other safety features are necessary. U.S. Pat. No. 4,665,117 describes the use of propylene oxide at 150° C. At this temperature, propylene oxide will be in the gaseous phase. Under these operating conditions, more than stoichiometric amounts of propylene oxide are required to carry the reaction to completion because propylene oxide will escape from the reaction mixture and this requires additional handling of the excess propylene oxide.

With the movement in the plastics industry to remove heavy metals, liquid calcium-zinc stabilizers are desirous, but not practical, as replacements for barium-cadmium or barium-zinc. Low metal concentrations, poor compatibility, haziness in clear products and plate out during processing in PVC have severely limited the universal acceptance of calcium based liquid stabilizer compositions. Problems are encountered in the stability of these compositions upon standing or storage. Storage stability is due to the incompatibility among the metal salts employed in the composition and is exhibited by increased turbidity, viscosity, or insoluble solids over time. As a result, the liquid calcium compositions are no longer homogeneous or readily pourable and must be specially treated in order to be used. U.S. Pat. No. 5,322,872 is directed to stabilized compositions of mixed metal carboxylates having improved storage stability. According to this patent, a complexing agent is added to the mixed metal carboxylate in order to improve shelf stability. Complexing agents disclosed in this patent include phosphines, phosphites, aromatic cyanides, aromatic hydroxy compounds, oximes and other compounds. U.S. Pat. Nos. 5,830,935 and 5,859,267 have also issued as directed to processes for improving basic metal salts and stabilizing halogen-containing polymers therewith.

Notwithstanding the state of the art as exemplified by the above patents, there is a need for further improvements in making shelf stable compositions of overbased alkaline earth metal carboxylates and in methods for their use in stabilizing halogen-containing polymers.

SUMMARY

The present invention relates to a shelf stable haze free liquid of an overbased alkaline earth metal salt of a fatty acid. In a preferred form, these liquids contain an alkaline earth metal carbonate, an alkaline earth metal carboxylate of a fatty acid, a liquid hydrocarbon, and an aliphatic alcohol having at least 8 carbon atoms. These liquids are referred to sometimes hereinafter more simply as "overbased alkaline earth metal salt(s)" or "overbased alkaline earth metal carboxylate(s)/carbonate(s)". Liquid overbased calcium and barium salts are preferably provided and, in a preferred form of the invention, the liquids are essentially free of a phenol or a phenolic derivative.

The invention also relates to a process for preparing the shelf stable haze free liquid of an overbased alkaline earth metal salt of a fatty acid. The process involves reacting an alkaline earth metal base and a fatty acid with an equivalent ratio of metal base to fatty acid being greater than 1:1 in the presence of a liquid hydrocarbon. A surfactant and catalyst are used to promote the reaction. The mixture is acidified, preferably by carbonation, to produce an amorphous alkaline earth metal carbonate. During carbonation, a dispersion of alkaline earth metal base, a liquid hydrocarbon, and an aliphatic alcohol having at least 8 carbon atoms, is added in relative amounts to produce a stable haze free liquid reaction product. Water is removed from the reaction product to obtain a shelf stable haze free liquid overbased alkaline earth metal salt.

It has been found important during carbonation to add the dispersion of metal base, liquid hydrocarbon and aliphatic alcohol in relative amounts at a controlled rate to produce the stable haze free reaction product. There are a number of reasons which are believed to contribute to the formation of a stable haze free liquid which is then filterable to remove impurities and byproducts of the reaction. Up to the discoveries made in accordance with the principles of this invention, it was not considered possible to make in a practical or commercial operation an overbased calcium fatty acid salt, for example, that may be filtered at commercial or practical rates to remove unwanted impurities and byproducts of the reaction to produce a shelf stable haze free liquid. In contrast, it has been found that by the continuous addition of the dispersion or slurry of base during carbonation, such results are achievable. It is believed that the metal base slurry prevents the formation of undesirable calcium carbonate crystals or byproducts in the desired overbased metal salt. These undesirable moieties prevent the formation of stable haze free products which are filterable. In other words, the metal base slurry is added at a controlled rate which does not exceed the rate of the desired product-forming reaction. The reaction is controlled by continuous or incremental addition of the metal base to make the calcium ions immediately available for the desired reaction as opposed to allowing the metal base, for example lime, to react and form a byproduct. Excessive byproduct or lime coated with calcium carbonate is believed to render the liquid product unfilterable. Using this procedure, the pH is controlled during the reaction so that the fatty acid is neutralized and the pH rises to about 10–12 with the continued addition of base to produce dissolved metal ion which reacts with $CO_2$ during carbonation to produce the desired product. It is believed if the reaction rate is not controlled, and the base is not dissolved, then solid base reacts or is coated with calcium carbonate to form undesirable byproducts. The formation of undesirable byproducts of the reaction renders the final product unstable and unfilterable.

The haze free liquids of the overbased alkaline earth metal fatty acid salts are suitable for use in making mixed metal stabilizer compositions with zinc, cadmium or alkyltin carboxylates. Other metal compound stabilizers that are well known may be used where the metal component can also be barium, calcium, strontium, lead, bismuth or antimony, and mixtures thereof. The mixed metal stabilizer compositions provide heat and/or light stability to vinyl halide resins such as polyvinyl chloride (PVC), and the like.

A number of benefits are obtained by the products and processes of this invention. Improvements in shelf stability of liquid overbased alkaline earth metal fatty acid salts are achieved. In particular, shelf stabilities are achieved with the liquids being free of phenol and phenolic derivatives such as phenolic reaction products. This is an especially desirable advantage in view of the efforts of the trade to reduce or eliminate such phenolic products because of environmental concerns. Also, as developed above, such phenols are a source of color development. In addition, enhanced shelf stability for the liquid overbased calcium fatty acid carboxylates and mixed metal stabilizer compositions of the invention have been demonstrated over presently commercially available products. In particular, presently available liquid overbased calcium fatty acid carboxylates exhibit the development of turbidity or haze, whereas the liquid compositions of this invention remain stable over extended periods of time. Therefore, the haze free liquids of this invention allow easy handling, storage and filtration. Furthermore, when the mixed metal stabilizer systems containing liquid overbased barium or calcium carboxylates are employed in vinyl halide polymers, they exhibit better compatibilities with improvements in thermal stability, clarity and plate out resistance.

The above advantages, benefits and further understanding of this invention will be apparent with reference to the following detailed description and preferred embodiments.

DETAILED DESCRIPTION AND PREFERRED EMBODIMENTS

A. Shelf Stable Haze Free Liquids of Overbased Alkaline Earth Metal Salts

In one preferred form of the invention, the shelf stable haze free liquid of an overbased alkaline earth metal salt of a fatty acid comprises
- an alkaline earth metal carbonate,
- an alkaline earth metal carboxylate of a fatty acid,
- a liquid hydrocarbon, and
- an aliphatic alcohol having at least 8 carbon atoms, with the liquid being preferably free of a phenol or a phenolic derivative such as a phenolic reaction product.

In another form of the invention, the alkaline earth metal sulfate, sulfide or sulfite may be formed instead of the carbonate where the acidic gas used in the process is sulfur dioxide, sulfur trioxide, carbon disulfide, or hydrogen sulfide.

The fatty acid of the overbased liquid carboxylate is generally a $C_{12}$–$C_{22}$ fatty acid, including, for example, lauric, myristic, palmitic, stearic, archidic and behenic, among the saturated fatty acids. Unsaturated fatty acids include palmitoleic, oleic, linoleic, and linolenic. Among these fatty acids, oleic is presently preferred in preparing the overbased liquid carboxylates.

The alkaline earth metal of the salt is selected from the group consisting of calcium, barium, magnesium and strontium. For example, shelf stable haze free overbased calcium oleates have been prepared. These overbased calcium salts contain calcium carbonate, calcium oleate, a liquid hydrocarbon diluent and an aliphatic alcohol having at least 8 carbon atoms.

In a broad form of the invention, it is important to have an aliphatic alcohol having at least 8 carbon atoms, more preferably an alcohol having 8 to 14 carbon atoms, such as, isodecanol, dodecanol, octanol, tridecanol and tetradecanol. Isodecanol is presently preferred. It has been found that when a higher aliphatic alcohol is employed in making the overbased product, phenol may be excluded from the reaction as a promoter. This is a particularly advantageous feature of the invention where it is undesirable to have a phenol or phenolic reaction product involved in the manufacture or use of the overbased liquid.

In another form of the invention, the liquid overbased alkaline earth salt of the fatty acid is believed to be a thermodynamically stable microemulsion. The microemulsion has micells and a continuous phase. The micells consist of an alkaline earth metal carbonate and an alkaline earth metal carboxylate of the fatty acid. The continuous phase of the microemulsion consists of the liquid hydrocarbon and the higher aliphatic alcohol.

Haze free liquids of the overbased metal salts have been prepared containing at least 4% by weight or more of the alkaline earth metal up to about 36% by weight. In the case of the overbased calcium salts, up to about 13–15% by weight calcium are produced and, for barium salts, up to about 36% by weight barium may be produced. In the preparation of higher overbased products, for example, containing about 13–15% by weight metal, it has been found suitable to use a glycol or a glycol ether along with the higher aliphatic alcohol. A glycol or glycol ether may be selected from the group consisting of diethylene glycol monobutyl ether (butyl Carbitol®), triethylene glycol, dipropylene glycol, diethylene glycol monomethyl ether, ethylene glycol monobutyl ether, and mixtures thereof.

B. The Basic Process and Critical Features

The process of the present invention for preparing a shelf stable haze free liquid of an overbased alkaline earth metal salt of a fatty acid comprises reacting an alkaline earth metal base and a fatty acid with an equivalent ratio of metal base to the fatty acid being greater than 1:1 in the presence of a mixture of liquid hydrocarbon. A surfactant and catalyst promote the reaction. The mixture is acidified and preferably carbonated to produce amorphous alkaline earth metal carbonate. During carbonation, a dispersion is added containing alkaline earth metal base, liquid hydrocarbon and an aliphatic alcohol having at least 8 carbon atoms in relative amounts at a controlled rate of base addition to produce a stable haze free liquid reaction product. Water is removed from the reaction product to produce a shelf stable haze free liquid overbased alkaline earth metal salt. Generally, it is preferred that the entire process be conducted in the absence of free oxygen and, for this purpose, an atmosphere of nitrogen is used.

As developed above, one of the important features of the method is the step of adding during carbonation a dispersion of alkaline earth metal base, liquid hydrocarbon and an aliphatic alcohol having at least 8 carbon atoms at a controlled rate of base addition to produce the stable haze free liquid. It has been found that the addition of a dispersion of the base in the liquid hydrocarbon and aliphatic alcohol protects or passivates the base, thereby enabling the formation of a stable haze free liquid reaction product. By protecting or passivating the base, carbonation proceeds to produce amorphous alkaline earth metal carbonate. Unexpectedly, the reaction proceeds without the need to remove water during the reaction and results in a very stable haze free liquid reaction product. At the end of the reaction, water is removed, preferably to the level of less than 1%, more preferably less than 0.3% or 0.1%, in the obtainment of the shelf stable liquid overbased salt. The removal of water which is added during the reaction or formed by the reaction is necessitated because it forms a separate phase which impedes either the product of the reaction or the formation of a shelf stable haze free liquid.

Other features of the method include filtering the product of the reaction to produce a shelf or thermodynamically stable liquid at a product filtration rate of at least about 300 ml per 10 minutes. In a preferred form of the invention, the product which is produced is filterable to remove unwanted byproducts and enhance the shelf stability of the overbased liquid. For example, with a Buchner funnel having a 15 cm diameter under vacuum of about 25–30 inches Hg with a Whatman No. 1 filter and a diatomaceous filtering aid (Celite® 512–577), the product is filterable at satisfactory rates. One of the important discoveries of the method of this invention is the ability to filter the reaction product to form a stable haze free liquid at filtration rates which heretofore were unachievable. This was especially the case when higher levels of metal content in the overbased liquids were desired, especially overbased calcium liquids. Thus, filtration removes undesirable impurities including silica, iron oxide and other metal species, unreacted calcium hydroxide, calcium carbonate, and other oxides which may contribute to lack of stability. These byproducts or impurities may comprise up to about 6% of byproduct of the reaction.

Throughout this specification and claims, the term "basic" or "overbased" as applied to the alkaline earth metal salts is used to refer to metal compositions wherein the ratio of total metal contained therein to the fatty acid moieties is greater than the stoichiometric ratio of the neutral metal salt. That is, the number of metal equivalents is greater than the number of equivalents of the fatty acid. In some instances, the degree to which excess metal is found in the basic metal salt is described in terms of a "metal ratio". Metal ratio as used herein indicates the ratio of total alkaline earth metal in the oil-soluble composition to the number of equivalents of the fatty acid or organic moiety. The basic metal salts often have been referred to in the art as "overbased" or "superbased" to indicate the presence of an excess of the basic component.

The process of the present invention may be used to prepare shelf stable liquids of the alkaline earth metal carboxylates of the fatty acids. As stated above, the method may be practiced without the use of phenol promoter or phenolic reaction product. Therefore, liquid overbased barium fatty acid carboxylates have been made without the need for a phenol or phenolic reaction product in order to achieve a shelf stable haze free liquid. In the case of liquid overbased calcium fatty acid carboxylates, shelf stable haze free products are obtained without a phenol where the aliphatic alcohol having at least 8 carbon atoms is employed.

The alkaline earth metal bases utilized as a reaction component may be derived from any alkaline earth metals and, of these, calcium and barium bases are particularly preferred. The metal bases include metal oxides and hydroxides and, in some instances, the sulfides, hydro sulfides, etc. While a phenolic component or reactant may preferably be excluded from a reaction, in the case of liquid overbased calcium products, the phenol or alkyl phenol may be included to yield liquid overbased products. As stated above, the fatty acids, or mixtures thereof, as identified above may be used in the reaction mixture. For example, a surfactant that facilitates the reaction is the alkaline earth metal carboxylate of the fatty acid that is formed in situ. Other surfactants may be included, for example, general purpose surface active agents identified under the trademark Tween which are polyoxyethylene derivatives of fatty acid partial esters of sorbitol anhydrides, particularly mono- and di-oleates of the ethoxylated sorbitol, and polyisobutylene succinic acid. Furthermore, it is desirable to include a catalyst to facilitate the speed of the reaction such as propionic acid, citric acid, acetic acid and adipic acid. The hydrocarbon liquid employed in the process and the liquid reaction products generally includes any hydrocarbon diluent. Most generally, the liquid hydrocarbon is selected from the group of an oil, mineral spirits and non-aromatic hydrocarbons.

C. Amounts of Reactants and Catalysts

The amount of alkaline earth metal base utilized in the preparation of basic salts is an amount which is more than one equivalent of the base per equivalent of fatty acid or organic moiety, and more generally, will be an amount sufficient to provide at least three equivalents of the metal base per equivalent of the acid. Larger amounts can be utilized to form more basic compounds, and the amount of metal base included may be any amount up to that amount which is no longer effective to increase the proportion of metal in the product. When preparing the mixture, the amount of fatty acid and the alcohol included in the mixture is not critical except that the ratio of equivalents of the metal base of the combination of the other components in the mixture should be greater than 1:1 in order to provide a basic product. More generally, the ratio of equivalents will be at least 3:1. In those instances where phenol may be present in making an overbased calcium, the ratio of equivalents of monocarboxylic acid to phenol should be at least about 1.1:1; that is, the monocarboxylic acid is present in excess with respect to the phenol.

The ranges of hydrocarbon oil, aliphatic alcohol (preferably isodecanol), butyl Carbitol and triethylene glycol have been selected such that, in the presence of the alkaline earth fatty acid salt (i.e. Ca oleate) which acts as a primary surfactant, the mixture forms a stable inverse microemulsion of the metal carbonate, water, and surfactant (internal phase) and surfactant, cosurfactant, and hydrocarbon (external continuous phase).

The acceptable ratios of hydrocarbon oil to cosurfactant aliphatic alcohol (isodecanol) are about 2:1 to about 4:1, with about 2:1 preferred. The glycol ethers may be used at about 1–15% of the final product, butyl Carbitol preferably at about 6%, and triethylene glycol at about 0–2%, preferably at about 0.6%.

The lime slurry which is added to the oleic acid in the reaction is formulated to be an easily pumpable mixture with the general composition of about 40–50% lime, about 25–40% hydrocarbon oil, about 10–25% isodecanol, and about 0–10% butyl Carbitol. The butyl Carbitol amount that is needed to make a pumpable slurry increases as the % lime in the slurry increases.

The reaction mixture for an overbased calcium oleate, after addition of the slurry and carbonation with carbon dioxide, preferably has the following composition ranges:

| | |
|---|---|
| Ca oleate (surfactant) | about 15–30% |
| Ca carbonate | about 9–35% |
| Hydrocarbon oil | about 30–35% |
| Isodecanol (cosurfactant) | about 15–18% |
| Butyl Carbitol | about 4–6% |
| Triethylene glycol | about 0–0.8% |

The catalyst, propionic acid or a lower aliphatic mono, di, or tricarboxylic acid is used in the amount of about 0–0.1% of the final reaction mixture.

Substitution of magnesium, strontium, or barium for calcium in the overbased salt is done on an equivalent basis of the metal hydroxide. On the basis of the final reaction mixture, the following amounts may be used:

| | |
|---|---|
| $Ca(OH)_2$ (lime) | about 15–30% |
| $Mg(OH)_2$ | about 12–24% |
| $Sr(OH)_2$ | about 25–50% |
| $Ba(OH)_2$ | about 35–50% |

The step of carbonation involves treating the mixtures described above with an acidic gas in the absence of free oxygen until the titratable basicity is determined using phenolphthalein. Generally, the titratable basicity is reduced to a base number below about 10. The mixing and carbonation steps of the present invention require no unusual operating conditions other than preferably the exclusion of free oxygen. The base, fatty acid and liquid hydrocarbon are mixed, generally heated, and then treated with carbon dioxide as the acidic gas, and the mixture may be heated to a temperature which is sufficient to drive off some of the water contained in the mixture. The treatment of the mixture with the carbon dioxide preferably is conducted at elevated temperatures, and the range of temperatures used for this step may be any temperature above ambient temperature up to about 200° C., and more preferably from a temperature of about 75° C. to about 200° C. Higher temperatures may be used such as 250° C., but there is no apparent advantage in the use of such higher temperatures. Ordinarily, a temperature of about 80° C. to 150° C. is satisfactory.

By the term "acidic gas" as used in this specification and in the claims is meant a gas which upon reaction with water will produce an acid. Thus, such gases as sulfur dioxide, sulfur trioxide, carbon dioxide, carbon disulfide, hydrogen sulfide, etc., are exemplary of the acidic gases which are useful in the process of this invention. Of these acids, sulfur dioxide and carbon dioxide are preferred, and the most preferred is carbon dioxide. When carbon dioxide is used the alkaline earth carbonate is formed. When the sulfur gases are used, the sulfate, sulfide and sulfite salts are formed.

D. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C=CHCl$ to polyvinyl chloride ($CH_2CHCl$—) wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

Metal compound heat stabilizers of vinyl halide resin compositions are well known. These metal compounds serve to capture HCl liberated during heat processing of the vinyl halide resin composition into its final shape. The metal can be lead, cadmium, barium, calcium, zinc, strontium, bismuth, tin, or antimony, for example. The stabilizers are usually metal salts of a carboxylic acid, advantageously of a $C_8$–$C_{24}$ carbon chain link monocarboxylic acid such as lauric, oleic, stearic, octoic, or similar fatty acid salts. Metal salts of alkyl phenates may be used. Mixed metal salts of such acids, and their preparation, are familiar to those skilled in the art to which this present invention pertains. Mixed metallic carboxylates involving calcium/zinc or barium/zinc blends alone and in combination with other stabilizers or additives such as beta-diketones, phosphite salts and phenolic antioxidants have been used. The metal stabilizer is a mixed metal salt of a carboxylic acid. Mixed metal salts of such acids, and their preparation, are also familiar to those skilled in the art to which this present invention pertains.

E. End Uses for the Stabilzers

The liquid stabilizers or mixed metal stabilizers of this invention may be used in a number of end products. Examples include: wall covering, flooring (vinyl tile and inlay), medical devices, dip coating, chair mat, banner film, pigment dispersion, vinyl siding, piping, fuel additive, cosmetic, ceiling tile, roofing film, wear layer, play balls or toys, teethers, fencing, corrugated wall panels, dashboards, and shifter boots.

The following Examples illustrate the preparation of the shelf stable haze free liquids of the overbased salts in accordance with the method of the present invention, but these examples are not considered to be limiting the scope

EXAMPLE 1
10% Overbased Calcium Oleate/Carbonate

A phenol-free 10% overbased calcium oleate/carbonate was prepared according to this Example. A mixture of 308.42 g of oleic acid (1.100 moles), 213.15 g mineral oil, 154.14 g of isodecyl alcohol, 63.08 g of butyl Carbitol, 8.70 g of triethylene glycol, 26.97 g of water and 0.87 g of propionic acid was heated to 190° F., with stirring, under a nitrogen atmosphere. To the stirred mixture there was continuously added a dispersion comprised of 38.98 g mineral oil, 13.86 g isodecyl alcohol, 3.71 g butyl Carbitol and 43.28 g of lime (0.5498 moles) for about 33 minutes to produce a solution of calcium oleate in the mixture. The dispersion was added at a rate of about 3 g per minute. At this point in the reaction, the mixture tested basic with phenolphthalein (about 10–12 pH). Then, to the stirred mixture there was continuously added, over a period of about 3 hours and 56 minutes, a dispersion comprised of 276.25 g mineral oil, 98.23 g isodecyl alcohol, 26.31 g butyl Carbitol and 306.75 g lime (3.897 moles) while the mixture was being treated with carbon dioxide at 1.5 SCFH at 195–200° F. The dispersion was also added at a rate of about 3 g per minute. The basicity of the reaction was checked to maintain the basicity during the reaction. When the reaction mixture tested nearly neutral to phenolphthalein, the carbon dioxide addition was discontinued. The reaction mixture was then heated to 300° F. and a total of 99.36 g of water was removed via a Dean-Stark trap. The resulting product mixture was stirred and 24.00 g of filter aid (diatomaceous earth) was added. The product mixture was filtered with suction, as stated above in the description, at about 300 ml per 10 minutes, yielding a clear, amber, mobile liquid filtrate of overbased calcium oleate/carbonate which remained clear upon cooling to room temperature. The filtrate was analyzed to contain 10.4% Calcium by weight.

EXAMPLE 2
14% Overbased Calcium Oleate/Carbonate

A phenol-free overbased calcium oleate/carbonate containing 14% calcium by weight was made according to this Example. In a 3-liter resin kettle equipped with an overhead stirrer, two gas inlet tubes, a thermocouple, heating mantle and Dean-Stark trap with condenser, was added 1700 g of a 9.89% overbased calcium oleate/carboxylate made by the method of the previous example and 42.5 g of deionized water. The mixture was heated with stirring under a nitrogen atmosphere to a temperature of 195° F., and a slurry containing 385 g of hydrated lime (94% calcium hydroxide), 231 g of hydrocarbon oil, 96.25 g of isodecyl alcohol, and 57.75 g of butyl Carbitol was added at a rate of 3.42 g per minute over a 3 hour 45 minute period. After 5 minutes of slurry addition, carbon dioxide was added to the reaction at a rate of 1.2 standard cubic feet per hour. During the carbonation, a temperature of 195–200° F. was maintained and pH was monitored as in Example 1.

After the slurry addition was finished, the carbon dioxide addition was continued until the reaction mixture was neutral, as shown by a colorless sample when tested with phenolphthalein. The reaction mixture was then heated to 300° F. and both the water added and the water produced in the reaction was removed via the Dean-Stark trap. To the dehydrated reaction product was added 75 g of diatomaceous earth and the product was filtered with suction, as above in Example 1, yielding a clear, amber, mobile liquid filtrate of overbased calcium oleate/carboxylate which remained clear on cooling to room temperature. The filtrate was analyzed to contain 14.5% calcium by weight.

Shelf Stable Haze Free Liquid Tests
Shelf Stability of the Phenol-Free Liquid Overbased Calcium Carboxylate/Carbonate of Example 1

Shelf stability of the phenol-free liquid overbased calcium carboxylate/carbonate of Example 1 (referred to hereinafter as New Calcium) was measured using a turbidity meter over a period of 60 days in order to study its shelf stability properties. The Old Calcium referred to hereinafter is a formerly commercially available overbased calcium carboxylate containing 14% Ca (Lubrizol's product LZ 2118, OMG Plastistab 2118).

The following Table I summarizes the results:

TABLE I

|  | 1 Day | 7 Days | 10 Days | 22 Days | 60 Days |
|---|---|---|---|---|---|
| Stabilizer containing New Calcium | 7.8 | 7.7 | 8.0 | 7.7 | 7.5 |
| Stabilizer containing Old Calcium | >200 | >200 | >200 | >200 | >200 |

Turbidity readings were measured in Jackson Turbidity Units (JTU). The turbidity observation between 1–30 indicates that the product is free from haze, and the observation above 30 to 200 JTU indicates that the product is hazy in nature. If the turbidity observation stays constant over a period of time, this means that the product possesses good shelf stability. This means that the product does not pick up any haze or undergo change in physical appearance over a period of time.

The data of Table I shows that the New Calcium possessed good shelf stability over a 60-day period, whereas the commercially available Old Calcium is hazy in nature.
Shelf Stability of Mixed Metal Stabilizer of Phenol-Free Overbased Calcium Carboxylate/Carbonate and Zinc Carboxylate (Calcium/Zinc Stabilizer)

Shelf stability of mixed metal calcium/zinc stabilizers containing New Calcium (Example 1) and Old Calcium was also monitored over a period of 24 days as shown in Table II. The stabilizer formulation contained 5% Ca, 1.2% Zn (zinc octoate), 3.5% P (diphenyl isodecyl phosphite), 5% carboxylic acid (oleic acid),3% anti-oxidant, 3% β-diketone (dibenzoyl methane) and diluent.

TABLE II

|  | 1 Day | 4 Days | 7 Days | 10 Days | 24 Days |
|---|---|---|---|---|---|
| Stabilizer containing New Calcium | 23.2 | 25.1 | 26.2 | 24.4 | 24.7 |
| Stabilizer containing Old Calcium | >200 | >200 | >200 | >200 | >200 |

The data illustrates that incorporation of New Calcium, versus Old Calcium, makes the mixed metal stabilizer shelf stable and haze free.

The above shelf stability tests were repeated by incorporating the New Calcium into a second stabilizer formulation. Shelf stability and clarity of a calcium/zinc stabilizer containing New and Old Calcium was monitored over a 24-day period, and the results are shown in Table Ill. Stabilizer formulation contained 5% Ca, 1.2% Zn (zinc octoate), 3.4% P (diphenyl decyl phosphite) 6% carboxylic acid (3% oleic acid/3% benzoic acid), 3% nonyl phenol as an anti-oxidant, 2% β-diketone (octyl benzoyl methane) and diluent.

TABLE III

|  | 1 Day | 4 Days | 7 Days | 10 Days | 24 Days |
|---|---|---|---|---|---|
| Stabilizer containing New Calcium | 25.1 | 26.3 | 28.1 | 26.5 | 26.8 |
| Stabilizer containing Old Calcium | >200 | >200 | >200 | >200 | >200 |

Again, the data illustrates that the New Calcium produces a shelf stable haze free mixed metal stabilizer versus the Old Calcium.

Shelf Stability of Mixed Metal Stabilizer of Overbased Calcium/Tin Carboxylate Stabilizers (Calcium/Tin Stabilizer)

Shelf stability of a calcium/tin stabilizer containing New Calcium (Example 1) and Old Calcium was monitored over a period of 25 days as shown in Table IV. Stabilizer formulation contained 5% Ca, 1.5% Sn (tin maleate), 3% P (diphenyl decyl phosphite), 5% carboxylic acid (oleic acid), 2% anti-oxidant (bisphenol-A), 3%-diketone (dibenzoyl methane) and diluent.

TABLE IV

|  | 1 Day | 4 Days | 7 Days | 11 Days | 25 Days |
|---|---|---|---|---|---|
| Stabilizer containing New Calcium | 52 | 54 | 58 | 61 | 62 |
| Stabilizer containing Old Calcium | >200 | >200 | >200 | >200 | >200 |

The data illustrates that the incorporation of New Calcium, versus Old Calcium, makes the stabilizer shelf stable.

Performance Comparisons: Thermal Degradation of PVC

The New Calcium (Example 1) and Old Calcium were incorporated into mixed metal stabilizer compositions for the purpose of observing their relative rate of thermal degradation in PVC. The stabilizer compositions are as follows:

| Stabilizer formulation | A | B |
|---|---|---|
| New Calcium | 5.5% Ca | — |
| Old Calcium (2118) | — | 5.5% Ca |
| Zinc carboxylate | 1.2% Zn | 1.2% Zn |
| Organic Phosphite | 3.0% P | 3.0% P |
| Carboxylic Acid | 4.0% | 4.0% |
| Anti-oxidant | 3.0% | 3.0% |
| Beta Diketone | 3.0% | 3.0% |
| Diluent | as needed | as needed |

The performances of these stabilizers A and B were observed in a PVC formulation containing 100 parts of PVC resin (K value 66), 30 parts phthalate plasticizer, 3 parts of epoxidized soybean oil and 2 parts of either stabilizer A or B.

Stabilized PVC compounds were then milled at 350–360° F. for 5 minutes at 25 mil thickness. The thermal stability was carried out at 375° F. over 56 minutes. Yellowness [+b chromaticity of CIELAB color space (Commission Internationale de l'Eclairage) developed in 1976] was measured with a Minolta calorimeter. The yellowness values of the rate of thermal degradation are shown in the following Table V.

The PVC formulation containing the stabilizer with the New Calcium (A) develops color at a slower rate than the PVC formulation using the stabilizer with the Old Calcium (B).

TABLE V

| Time (minutes) | New Calcium A | Old Calcium B |
|---|---|---|
| 7 | 9.68 | 10.11 |
| 14 | 10.52 | 10.68 |
| 21 | 11.76 | 11.54 |
| 28 | 15.25 | 14.89 |
| 35 | 18.39 | 19.59 |
| 42 | 38.57 | 47.77 |
| 49 | 46.69 | 56.92 |
| 56 | 60.11 | 69.33 |

Performance Comparisons: Clarity

The New Calcium (Example 1) and Old Calcium, along with a calcium carboxylate ($C_8$), were incorporated into mixed metal stabilizer compositions for the purpose of observing their influence on the clarity of the PVC application. The stabilizer compositions are as follows:

| Stabilizer Formulation | A | B | C |
|---|---|---|---|
| New Calcium | 5.5% | — | — |
| Old Calcium | — | 5.5% | — |
| Calcium Carboxylate ($C_8$) | — | — | 5.5% Ca |
| Zinc carboxylate | 1.2% Zn | 1.2% Zn | 1.2% Zn |
| Organic Phosphite | 3.4% P | 3.4% P | 3.4% P |
| Carboxylic Acid | 5.0% | 5.0% | 5.0% |
| Anti-oxidant | 3.0% | 3.0% | 3.0% |
| Beta Diketone | 2.0% | 2.0% | 2.0% |
| Diluent | as needed | as needed | as needed |

The relative degree of clarity of the 0.25 inch pressed PVC formulations containing either stabilizer A, B or C was observed after 5 minutes of exposure to 350° F. and 15,000 pounds pressure. The PVC formulation comprised of 100 parts PVC resin (K value 66), 30 parts phthalate plasticizer, 3 parts of epoxidized soybean oil and 2 parts of either stabilizer A, B or C.

The pressed PVC samples were placed vertically near printed material to determine the crispness of the print when looking through the press. Stabilizer A and B gave comparable crispness. However, both stabilizer A and B gave better clarity or crispness than stabilizer C.

Performance Comparisons: Plate Out

The New Calcium (Example 1) and Old Calcium along with a non-carbonated calcium carboxylate were incorporated into mixed metal stabilizer compositions for the purpose of observing their influence on the resistance to plate out of the stabilizer during processing of the vinyl formulation. The stabilizer compositions have been identified above as A, B and C with A containing the New Calcium, B containing the Old Calcium and C containing the non-carbonated calcium carboxylate.

Plate out is determined by introducing a red pigment into a PVC formulation containing the stabilizer and allowing the pigment to migrate from the formulation to the metal rolls of a two roll mill at 340° F. A white clean up compound is then placed onto the rolls and the degree of plate out is determined by the amount of red picked up by the clean up compound. The colorimeter assigns a numerical value on the CIElab scale for the degree of redness or plate out (+a).

| Red pigmented formulation: | | Clean up compound | |
| --- | --- | --- | --- |
| 100 | PVC resin | 100 | PVC resin |
| 40 | phthalate plasticizer | 40 | phthalate plasticizer |
| 8 | epoxidized soybean oil | 8 | epoxidized soybean oil |
| 0.2 | stearic acid | 0.2 | stearic acid |
| 2 | red 2B pigment | 4 | Titanium dioxide |
| 1.5 | stabilizer | 3 | lead phosphite |

The red formulation is milled for 4 minutes undisturbed after which the clean up compound is introduced and milled for three minutes undisturbed.

Colorimeter readings, +a value indicating increasing degree of red:

| Sample | a-value |
| --- | --- |
| A | −2.28 |
| B | −2.07 |
| C | +24.3 |

There is essentially no difference between the New and Old Calcium as far as plate out resistance. However, there is a significant difference between A and C where the New Calcium provides superior plate out resistance.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall within the scope of the invention.

What is claimed is:

1. A process for preparing a shelf stable haze free liquid of an overbased alkaline earth metal salt of a fatty acid comprising
    reacting an alkaline earth metal base and a fatty acid with an equivalent ratio of metal base to fatty acid being greater than 1:1 in the presence of liquid hydrocarbon,
    carbonating the mixture to produce amorphous alkaline earth metal carbonate,
    adding during carbonation a dispersion of alkaline earth metal base, a liquid hydrocarbon and an aliphatic alcohol having at least 8 carbon atoms in relative amounts at a controlled rate of alkaline earth metal base addition to produce a stable haze free liquid reaction product, and
    removing water from the reaction product to obtain a shelf stable haze free liquid overbased alkaline earth metal salt.

2. The process of claim 1 further comprising filtering the liquid reaction product to produce a thermodynamically stable liquid at a product filtration rate of at least about 300 ml per 10 minutes.

3. The process of claim 1 wherein said fatty acid is a $C_{12}$–$C_{22}$ fatty acid.

4. The process of claim 1 wherein said fatty acid is oleic acid.

5. The process of claim 1 wherein water is removed to provide a microemulsion product having less than about 1% by weight water of the total product.

6. The process of claim 1 wherein said alkaline earth metal is selected from the group consisting of calcium, barium, magnesium and strontium.

7. The process of claim 1 wherein said alkaline earth metal is calcium.

8. The process of claim 1 wherein the overbased salt is calcium oleate/carbonate.

9. The process of claim 1 to produce the overbased salt which is essentially free of a phenol or phenolic derivative.

10. The process of claim 1 wherein said aliphatic alcohol has 8 to 14 carbon atoms.

11. The process of claim 10 wherein the alcohol is isodecanol.

12. The process of claim 11 wherein the continuous phase further contains a glycol or a glycol ether.

13. The process of claim 12 wherein the glycol or glycol ether is selected from the group consisting of diethylene glycol monobutyl ether, triethylene glycol, dipropylene glycol, diethylene glycol monomethyl ether, ethylene glycol monobutyl ether, and mixtures thereof.

14. The process of claim 1 by reacting on the basis of the final reaction mixture an amount of an alkaline earth metal base selected from the group consisting of about 15–30% calcium hydroxide, about 12–24% magnesium hydroxide, about 25–50% strontium hydroxide, and about 35–50% barium hydroxide, and mixtures thereof.

15. The process of claim 14 wherein the alkaline earth metal base is calcium hydroxide and the fatty acid is oleic acid.

16. The process for preparing a shelf stable haze free liquid of an overbased calcium oleate/carbonate comprising
    reacting calcium hydroxide base and oleic acid with an equivalent ratio of the base to the acid being greater than 1:1 in the presence of a mixture of liquid hydrocarbon and catalyst,
    carbonating the mixture to produce amorphous calcium carbonate,
    adding during carbonation a dispersion of calcium hydroxide, liquid hydrocarbon and cosurfactant aliphatic alcohol having at least 8 carbon atoms in relative amounts at a controlled rate of calcium hydroxide addition to produce a stable haze free liquid reaction product, and
    removing water from the reaction product to provide a shelf stable haze free overbased calcium oleate/carbonate.

17. The process of claim 16 comprising the further step of filtering the liquid reaction product to remove byproducts or impurities.

18. The process of claim 16 which is conducted essentially free of a phenol or a phenolic derivative.

19. The process of claim 16 wherein the catalyst is selected from the group consisting of propionic acid, citric acid, acetic acid and adipic acid.

20. The process of claim 16 wherein the surfactant is calcium oleate borne by the reaction of the base and the oleic acid in situ.

21. The process of claim 16 wherein the cosurfactant is an aliphatic alcohol having 8 to 14 carbon atoms.

22. The process of claim 21 wherein the alcohol selected is isodecanol in the presence of diethylene glycol monobutyl ether and triethylene glycol.

23. The process of claim 21 wherein the haze free liquid calcium oleate is a microemulsion having amorphous calcium carbonate within the micelles of the microemulsion.

24. The process of claim 16 wherein after the addition of the dispersion and carbonation with carbon dioxide the mixture contains
    about 15–30% calcium oleate,
    about 8–35% calcium carbonate,
    about 30–35% hydrocarbon oil, about 15–18% idodecenol, and about 4–6% glycol or glycol ether.

25. The process of claim 24 wherein the dispersion contains about 40–50% calcium hydroxide, about 25–40% hydrocarbon oil, about 10–25% isodecanol and about 0–10% glycol or glycol ether.

26. The shelf stable haze free liquid prepared in accordance with the process of claim 1.

27. The shelf stable haze free liquid prepared in accordance with the process of claim 2.

28. The shelf stable haze free liquid prepared in accordance with the process of claim 3.

29. The shelf stable haze free liquid prepared in accordance with the process of claim 3.

30. The shelf stable haze free liquid prepared in accordance with the process of claim 5.

31. The shelf stable haze free liquid prepared in accordance with the process of claim 6.

32. The shelf stable haze free liquid prepared in accordance with the process of claim 7.

33. The shelf stable haze free liquid prepared in accordance with the process of claim 8.

34. The shelf stable haze free liquid prepared in accordance with the process of claim 9.

35. The shelf stable haze free liquid prepared in accordance with the process of claim 10.

36. The shelf stable haze free liquid prepared in accordance with the process of claim 11.

37. The shelf stable haze free liquid prepared in accordance with the process of claim 12.

38. The shelf stable haze free liquid prepared in accordance with the process of claim 13.

39. The shelf stable haze free liquid prepared in accordance with the process of claim 14.

40. The shelf stable haze free liquid prepared in accordance with the process of claim 15.

41. The shelf stable haze free liquid prepared in accordance with the process of claim 16.

42. The shelf stable haze free liquid prepared in accordance with the process of claim 18.

43. The shelf stable haze free liquid prepared in accordance with the process of claim 24.

44. The shelf stable haze free liquid prepared in accordance with the process of claim 25.

* * * * *

UNITED STATES PATENT AND TRADEMARK OFFICE
CERTIFICATE OF CORRECTION

PATENT NO. : 6,689,893 B2
DATED : February 10, 2004
INVENTOR(S) : James E. Reddy et al.

It is certified that error appears in the above-identified patent and that said Letters Patent is hereby corrected as shown below:

Column 8,
Line 25, change "$(CH_2CHCL-)$" to -- $(CH_2CHCL-)_n$ --

Column 10,
Line 65, change "Table I11" to -- Table III --

Column 11,
Line 22, change "3%-diketone" to -- 3% β –diketone --
Line 63, change "Minolta calorimeter" to -- Minolta colorimeter --

Column 14,
Line 66, change "about 8-35 %" to -- about 9-35 % --

Column 15,
Line 14, change "the process of claim 3" to -- the process of claim 4 --

Signed and Sealed this

Seventeenth Day of August, 2004

JON W. DUDAS
*Acting Director of the United States Patent and Trademark Office*